United States Patent
Herndon

(10) Patent No.: US 7,098,248 B2
(45) Date of Patent: Aug. 29, 2006

(54) BETA-ADRENERGIC BLOCKADE REVERSAL OF CATABOLISM AFTER SEVERE BURN

(75) Inventor: David S. Herndon, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 443 days.

(21) Appl. No.: 09/901,429

(22) Filed: Jul. 9, 2001

(65) Prior Publication Data

US 2003/0018084 A1 Jan. 23, 2003

(51) Int. Cl.
*A61K 31/135* (2006.01)

(52) U.S. Cl. ............... 514/651; 424/810; 530/350
(58) Field of Classification Search .......... 514/651; 424/810; 530/350
See application file for complete search history.

(56) References Cited

U.S. PATENT DOCUMENTS 5,260,066 A * 11/1993 Wood et al.
6,194,578 B1 * 2/2001 Griffith et al.
2001/0056068 A1 * 12/2001 Chwalisz et al.

FOREIGN PATENT DOCUMENTS

WO    WO 9604233    2/1996

OTHER PUBLICATIONS

Herndon et al, Lipolysis in burned patients . . . , Archives of Surgery, 1994, Vol. 129/12, pp. 13012–1305.*
Hart et al, Anticatabolism agter sever burn . . . , Database Caplus, AN 2001:119741, Abstract, Surg. Forum(2000), vol. 51, pp. 196–197.*

Baron et al., "Prolonged use of propranolol safety decreases cardiac work in burned children," *J. Burn Care Rehabil.*, 18:223–227, 1997.

Breitenstein et al., "Effects of beta–blockade on energy metabolism following burns," *Burns*, 16:259–264, 1990.

Chance et al., "Clenbuterol decreases catabolism and increases hypermetabolism in burned rats," *Journal of Trauma*, 31(3):365–379, 1991.

Hart et al., "Anticatabolism after sever burn: synergism between growth hormone and propranolol,"Abstract in *Surg. Forum*, 51:196–197, 2000.

Herndon et al., "Effect of propranolol administration on hermodynamic and metabolic responses of burned pediatric patients," *Ann. Surg.*208:484–492, 1988.

Herndon et al., "Lipolysis in burned patients is stimulated by the $\beta_2$receptor for catecholamines," *Arch. Surg.*, 129:1301–1305, 1994.

Maggi et al., "Beta–1 blockade decreases cardiac work without affecting protein breakdown or lipolysis in severely burned patients," Surgical Forum, 44(0):25–27, 1993.

Mangano et al., "Effect of atenolol on mortality and cardiovascular morbidity after noncardiac surgery. Multicenter Study of Perioperative Ischemia Research group," N. Engl. J. Med., 335:1713–1720, 1996.

Minifee et al., "Improved myocardial oxygen utilization following propranolol infusion in adolescents with postburn hypermetabolism," *Pediatr. Surg.*, 24:806–810, 1989.

* cited by examiner

*Primary Examiner*—Vickie Kim
(74) *Attorney, Agent, or Firm*—Fulbright & Jaworski L.L.P.

(57) ABSTRACT

Provided herein is a method of method of treating an individual having a severe burn, comprising the step of administering to said individual a pharmacologically effective dose of a beta-adrenergic antagonist.

11 Claims, 3 Drawing Sheets

BETA-ADRENERGIC BLOCKADE REVERSAL OF CATABOLISM AFTER SEVERE BURN

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the field of burn patient therapy. More specifically, the present invention relates to a method of β-adrenergic blockade reversal of catabolism after severe burn.

2. Description of the Related Art

The hypermetabolic response to severe burn is associated with increased energy expenditure and substrate release from protein and fat stores. After severe trauma, net protein catabolism is increased which leads to loss of lean body mass and muscle wasting.[1,2] Muscle proteolysis continues for at least 9 months after severe burn[3] which predisposes patients to delays in rehabilitation, and increased morbidity and mortality.[4]

Endogenous catecholamines are primary mediators of the hypermetabolic response to trauma or burn.[5,6] Shortly after severe trauma or burn, plasma catecholamine levels increase as much as 10-fold.[7,8] This systemic response to injury is characterized by development of a hyperdynamic circulation[9], elevated basal energy expenditure[10], and net skeletal muscle protein catabolism.[3,11]

Blockade of β-adrenergic stimulation after severe burn has been found to attenuate supraphysiologic thermogenesis[12], tachycardia[13], cardiac work[14], and resting energy expenditure.[15] Decreased cardiac morbidity and diminished overall mortality have been documented in non-trauma patients given β blockers for control of tachycardia after a major surgical procedure.[16]

The prior art is deficient in the lack of effective means of decreasing muscle protein catabolism in burn patients. The present invention fulfills these long-standing needs and desires in the art.

SUMMARY OF THE INVENTION

The present invention demonstrates that blockade of β-adrenergic stimulation with orally administered propranolol decreases resting energy expenditure and net muscle catabolism. Twenty-five acute, severely burned (>40% total body surface area) children were studied in a prospective, randomized trial. Thirteen of the subjects received oral propranolol for at least two weeks, and twelve served as non-treated controls. Propranolol was titrated to decrease resting heart rate 20% from the patient's baseline. Resting energy expenditure (REE) and skeletal muscle protein kinetics were measured before and after two weeks of β-blockade (or no therapy in non-treated controls). Body composition was measured serially throughout the hospital course. Control and propranolol subjects were statistically similar in age, weight, % total body surface area burned, %3$^{rd}$ degree, and time from injury.

During beta blockade, heart rates and resting energy expenditures of the propranolol group were lower than baseline and lower than those of the control group (p<0.05). Corresponding to the significant differences in heart rate and resting energy expenditure, muscle protein net balance improved 82% relative to pre-treated baseline in the subjects treated with propranolol while it decreased 27% in the non-treated control subjects (p<0.05). Fat free mass measured by whole body potassium counter did not change in the propranolol group, but decreased 9±2% in time control subjects (p<0.01). Thus, in pediatric burn victims, propranolol attenuates hypermetabolism and reverses muscle protein catabolism when administered for an extended period during the acute hospitalization.

In one embodiment of the present invention there is provided a method of treating an individual having a severe burn, comprising the step of administering to said individual a pharmacologically effective dose of a beta-adrenergic antagonist.

In another embodiment of the present invention there is provided a method of treating an individual having a severe burn, comprising the step of administering to said individual a pharmacologically effective dose of propranolol.

In yet another embodiment of the present invention there is provided a method of decreasing protein catabolism and increasing lean body mass in an individual, comprising the step of administering to said individual a pharmacologically effective dose of a beta-adrenergic antagonist.

Other and further aspects, features, and advantages of the present invention will be apparent from the following description of the embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

DETAILED DESCRIPTION OF THE INVENTION

Figure 1:
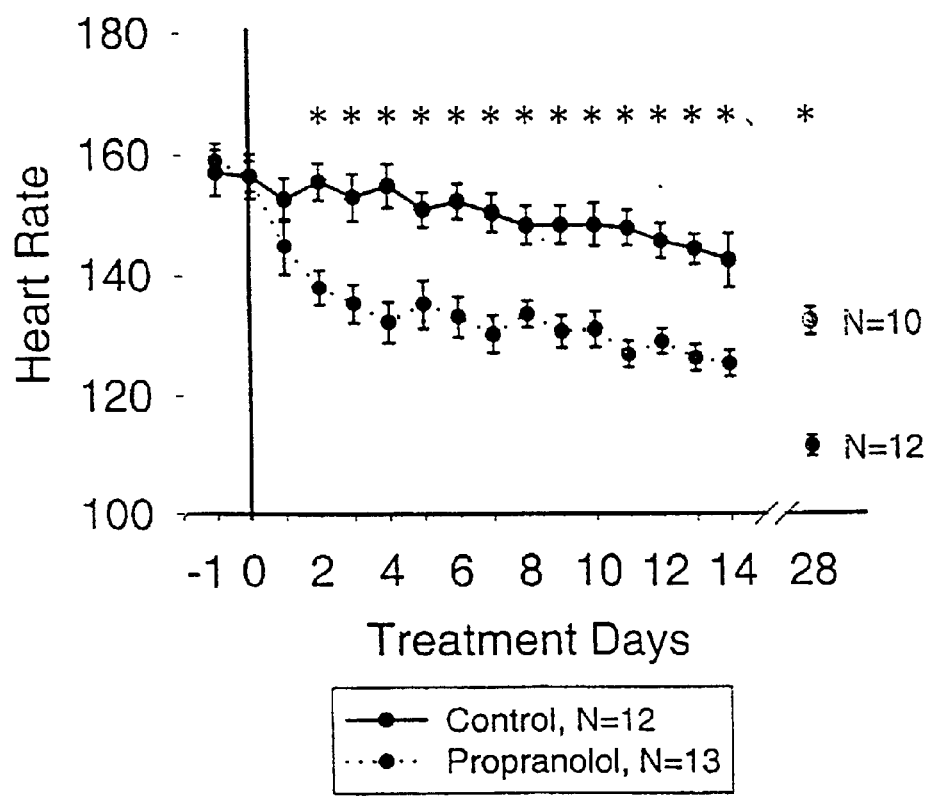
FIG. 1 depicts the average hourly heart rate. *p=0.03 vs. time control group by t-test. Data are presented as mean±SEM.

In one embodiment, the present invention is directed a method of treating an individual having a severe burn, comprising the step of administering to said individual a pharmacologically effective dose of a beta-adrenergic antagonist. Generally, the beta-adrenergic antagonist may be administered by any effective route. For example, the beta-adrenergic antagonist may be administered intravenously.

Preferably, the beta-adrenergic antagonist is administered in a dose that decrease heart rate in the individual by about 25%. A person having ordinary skill in this art would readily appreciate and recognize the various routes, schedules, regimens and amounts of the administration of beta-adrenergic antagonists in the methods of the present invention. For example, the beta-adrenergic antagonist maybe administered in a dose of from about 0.1 mg/kg of the body weight of the individual to about 10 mg/kg of the body weight of the individual. Although any beta-adrenergic antagonist may be useful in the claimed methods, representative beta-adrenergic antagonist include propranolol, timolol, nadolol, atenolol, metoprolol, esmolol, nipradilol, carvedilol and acebutolol.

In another aspect of this embodiment there is provided a method of treating an individual having a severe burn, comprising the step of administering to said individual a pharmacologically effective dose of propranolol. Preferably, the propranolol is administered intravenously and would be administered in a dose that decrease heart rate in said individual by about 25%. In this method, propranolol is administered in a dose of from about 0.1 mg/kg of the body weight of the individual to about 10 mg/kg of the body weight of the individual.

In another embodiment, the present invention is also directed to a method of decreasing protein catabolism and increasing lean body mass in an individual, comprising the step of administering to said individual a pharmacologically effective dose of a beta-adrenergic antagonist. Generally, the beta-adrenergic antagonist may be administered by any effective route. For example, the beta-adrenergic antagonist may be administered intravenously. Preferably, the beta-adrenergic antagonist is administered in a dose that decrease heart rate in the individual by about 25%. A person having ordinary skill in this art would readily appreciate and recognize the various routes, schedules, regimens and amounts of the administration of beta-adrenergic antagonists in this method of the present invention. For example, the beta-adrenergic antagonist maybe administered in a dose of from about 0.1 mg/kg of the body weight of the individual to about 10 mg/kg of the body weight of the individual. Although any beta-adrenergic antagonist may be useful in the claimed methods, representative beta-adrenergic antagonist include propranolol, timolol, nadolol, atenolol, metoprolol, esmolol, nipradilol, carvedilol and acebutolol.

The following examples are given for the purpose of illustrating various embodiments of the invention and are not meant to limit the present invention in any fashion.

EXAMPLE 1

Subjects

This study was approved by The University of Texas Medical Branch Institutional Review Board, and informed written consent was obtained from each patient's guardian. Inclusion criteria were: children <18 years of age, total body surface area (TBSA) burns of >40%, and transfer to the hospital within one week of injury. Patients with known history of asthma were excluded.

Within 48 hours of admission, each patient underwent burn wound excision and grafting with autograft and allograft skin. Patients returned to the operating room when autograft donor sites healed (6–10 days). Sequential staged surgical procedures for grafting were undertaken until the wounds were closed.

Each patient received nutrition via a naso-duodenal tube with Vivonex TEN (Sandoz Nutritional Corp., Minneapolis, Minn.). Daily caloric intake was given at a rate calculated to deliver 1500 kcal/m$^2$ total body surface area burned +1500 kcal/m$^2$ total body surface area. Feeding was started at admission and continued until the wounds were healed. Patients were at bed rest after excision and grafting procedures for 5 days. After this, patients ambulated daily until the next excision and grafting procedure.

EXAMPLE 2

Study Design

From January 1999 through December 1999, twenty-five subjects were enrolled into a prospective, randomized trial. Thirteen received propranolol and twelve served as non-treated controls. Enrollment was assigned by a random number generator scheme.

After the first surgical procedure, all subjects underwent metabolic examinations on the fifth postoperative day. Resting energy expenditure (REE) and net protein balance across the leg were measured as the main outcome variables. Additionally, all subjects underwent baseline whole body potassium scanning to determine fat-free mass. After the next operation, propranolol subjects began oral propranolol at 0.33 mg/kg every 4 hours (1.98 mg/kg/day). This dose was titrated to achieve a 25% decrease in heart rate from the subject's own 24 hour average heart rate immediately prior to drug treatment. Heart rate and blood pressure were monitored continuously throughout the study. With a fall in blood pressure below a mean pressure of 65 mmHg, the dose of propranol was held and/or decreased. The dose was then increased incrementally to meet study goals or a decrease in heart rate by 20% from established baseline levels as tolerated. Propranolol was given as scheduled during operative procedures.

Two weeks after treatment was started, a second series of metabolic and protein kinetic studies was performed. Subjects who received at least a four-week treatment course underwent a second whole-body potassium measurement. At discharge, subjects underwent body composition scanning by a dual image x-ray absorptiometry.

EXAMPLE 3

Vital Signs

Temperature, heart rate, systolic blood pressure, and diastolic blood pressure were measured hourly from a standard continuous bladder temperature monitor, ECG monitor, and arterial catheter. The average for each 24-hour period was determined. Heart rate comparisons were made between groups for the duration of study. Other analyses or changes with treatment were made between groups on the day of stable isotopic study.

EXAMPLE 4

Serum Glucose, Potassium, and Hormone Values

Serum glucose and potassium were determined on a Stat-5 analyzer (Novel Biomedical, Waltham, Mass.). Serum measurements of insulin-like growth factor-1 (IGF-1) (ethanol extraction), growth hormone, cortisol, and insulin were determined by ELISA or EIA (Diagnostic Systems Laboratories, Webster, Tex.). Samples obtained the morning of the stable isotopic studies were used for analysis between groups.

EXAMPLE 5

Infection

Infection was determined by the incidence of burn sepsis, as described previously.[17] This parameter was determined throughout hospitalization.

EXAMPLE 6

Energy Expenditure

Between midnight and 5 AM on the day of study, oxygen consumption ($\dot{V}O_2$), carbon dioxide production ($\dot{V}CO_2$), respiratory quotient (RQ) and resting energy expenditure (REE) were determined with a metabolic cart (Sensormedics Model 2900; Yorba Linda, Calif.) at 30° C. ambient room temperature during continuous feeding.

EXAMPLE 7

Stable Isotope Protocol

On postoperative day 5 after the first and third operations, all subjects underwent a 5-hour protein kinetic study in the fed state as previously described.[18] Briefly, a primed-constant infusion of L-[ring-$^2$H$_5$]-phenylalanine (Cambridge Isotopes; Andover, Mass.) was given intravenously for 5 hours (priming dose 2 μmol/kg followed by 0.08 μmol/kg/min). Vastus lateralis muscle biopsies were taken from the study leg 2 and 5 hours after commencement. Leg blood flow was determined by indocyanine green infusion into the femoral artery.

EXAMPLE 8

Analysis of Samples

The blood concentration of unlabeled phenylalanine and the enrichment of its isotopic counterpart were simultaneously determined by gas chromatography—mass spectrometry (GCMS) using the internal standard approach and N-methyl-N-(tert-butyldimethylsilyl)trifluoroacetamide, as previously described.[19] ICG concentrations were determined spectrophotometrically at λ=805 n m on a Spectronic 1001 (Bausch and Lomb, Rochester, N.Y.).

Muscle samples were stored at −70° C. Each was weighed and protein precipitated with 5% perchloric acid solution. An internal standard containing 5.9 μmol/L of [$^{13}$C$_6$] phenylalanine was added and thoroughly mixed. Enrichments of the bound protein precipitate were determined by comparing the measured M+5/M+3 isotopomer ratio of samples to a set of d$^5$-phenylalanine isotope dilution calibration standards.[18]

EXAMPLE 9

Calculations

Kinetic Models. 3-Pool Model: Cross-leg amino acid kinetics were calculated according to a three-compartment model described by Chinkes and Wolfe.[18]

Fractional Synthetic Rate of Muscle Protein. Skeletal muscle fractional synthetic rate was calculated from the determination of the rate of d5-labeled Phenylalanine incorporation into protein and the enrichment of the intracellular pool as the precursor as previously described.[19]

EXAMPLE 10

Body Composition

Determination of Fat-Free Mass using Potassium 40 Whole Body Counting. Fat-Free Mass was determined by Whole Body Potassium 40 ($^{40}$K) scintillation counting in a heavily shielded low background noise counting room, a 32 NaI detector array, and computed data analysis which has been validated for use in children.[20,21] The counting precision of the instrument used is <1.5%, which was calibrated daily using BOMAB Phantoms with simulated fat overlays. All studies were done after feedings and IV fluids were discontinued to minimize exogenous potassium contamination.

EXAMPLE 11

DEXA Scanning

Total body lean mass and fat mass were measured by dual image x-ray absorptometry. A Hologic model QDR-4500W DEXA (Hologic Inc, Waltham, Mass.) with the pediatric software package was used to measure body composition. This system has been shown to have minimal mean error in measuring fat-free mass in children.[22] To minimize systematic deviations, the system was calibrated daily against a spinal phantom in the anteroposterior, lateral, and single-beam modes.

EXAMPLE 12

Data Presentation and Statistical Analysis

Data are presented as means±SEM. All data were found to have equal variance and normality. Two-sided paired t-tests were used to compare data within groups. Comparisons between groups were made by unpaired t-tests. Fisher's exact test was used for frequency data. p<0.05 was considered statistically significant.

EXAMPLE 13

Results

Patient demographics are listed in Table 1. One of the twenty-five subjects chose not to participate in the stable isotope studies. Three subjects (2 control and 1 propranolol) were fully healed and discharged prior to receiving four weeks of treatment. These subjects did not receive a second whole body potassium counter study.

TABLE 1

Patient Demographics

| | Non-Treated Control | Propranolol |
|---|---|---|
| Age | 7.8 ± 1.4 | 6.6 ± 1.5 |
| Sex | 9 M/3 F | 7 M/5 F |
| Weight at admission (kg) | 36.7 ± 7.1 | 28.1 ± 6.0 |
| Body Surface Area (m$^2$) | 0.95 ± 0.14 | 0.83 ± 0.11 |
| Burn Size (% total body surface area burned) | 47 ± 4 | 57 ± 4 |
| % 3rd Degree | 39 ± 5 | 41 ± 5 |
| Time after burn at initial metabolic study | 10 ± 1 | 12 ± 3 |
| Time after burn at second metabolic study | 24 ± 2 | 29 ± 3 |

Data presented as mean ± SEM.

Propranolol decreased heart rate 20% compared with both the patient's own baseline, and with non-treated controls (p=0.03, FIG. 1). Propranolol doses required escalation from the initial starting dose of 0.33 mg/kg given enterally every 4 hours (1.98 mg/kg/day) to an average dose of 1.05±0.15 mg/kg every 4 hours (6.3 mg/kg/day) by the end of hospitalization. Blood pressures, temperature, and glucose values were not statistically different between groups. Serum potassium values were higher in the propranolol group (Table 2).

TABLE 2

Changes In Values From Baseline

| | Non-Treated Controls | Propranolol | p |
|---|---|---|---|
| Systolic blood pressure (mHg) | 1 ± 5 | −4 ± 5 | 0.56 |
| Diastolic blood pressure (mm/mHg) | −2 ± 5 | −5 ± 5 | 0.69 |
| Mean arterial pressure (mHg) | 6 ± 9 | 1 ± 8 | 0.70 |
| Temperature (° C.) | −0.6 ± 0.2 | −0.5 ± 0.2 | 0.52 |
| Potassium (mg/dl) | −0.1 ± 0.1 | 0.4 ± 0.2 | 0.05 |

TABLE 2-continued

Changes In Values From Baseline

| | Non-Treated Controls | Propranolol | p |
|---|---|---|---|
| Glucose (mg/dl) | −40 ± 16 | −30 ± 13 | 0.67 |
| Oxygen consumption | 25 ± 11 | −56 ± 22 | 0.002 |
| Carbon dioxide production | −8 ± 17 | −64 ± 22 | 0.045 |
| Respiratory quotient | −0.1 ± 0.1 | −0.1 ± 0.1 | 0.49 |
| Resting energy expenditure | 140 ± 67 | −422 ± 197 | 0.001 |
| Leg blood flow (ml/100 ml leg/min) | −242 ± 308 | −182 ± 148 | 0.54 |
| Insulin-like growth factor-1 (ng/ml) | 38 ± 15 | 38 ± 13 | 0.99 |
| Growth hormone (ng/ml) | 0.1 ± 1.0 | −1.1 ± 0.9 | 0.38 |
| Cortisol (μg/dl) | −6.7 ± 3.1 | −3.1 ± 2.2 | 0.34 |
| Insulin (μIU/ml) | 4.7 ± 23.4 | −29.4 ± 18.5 | 0.27 |

Resting energy expenditure (REE), oxygen consumption ($\dot{V}O_2$), and carbon dioxide production ($\dot{V}CO_2$) increased between metabolic studies in non-treated controls. In contrast, propranolol treated subjects experienced significant decreases in resting energy expenditure, oxygen consumption, and carbon dioxide production over this same time period compared to the non-treated group. Respiratory quotient did not change (Table 2).

Figure 2:
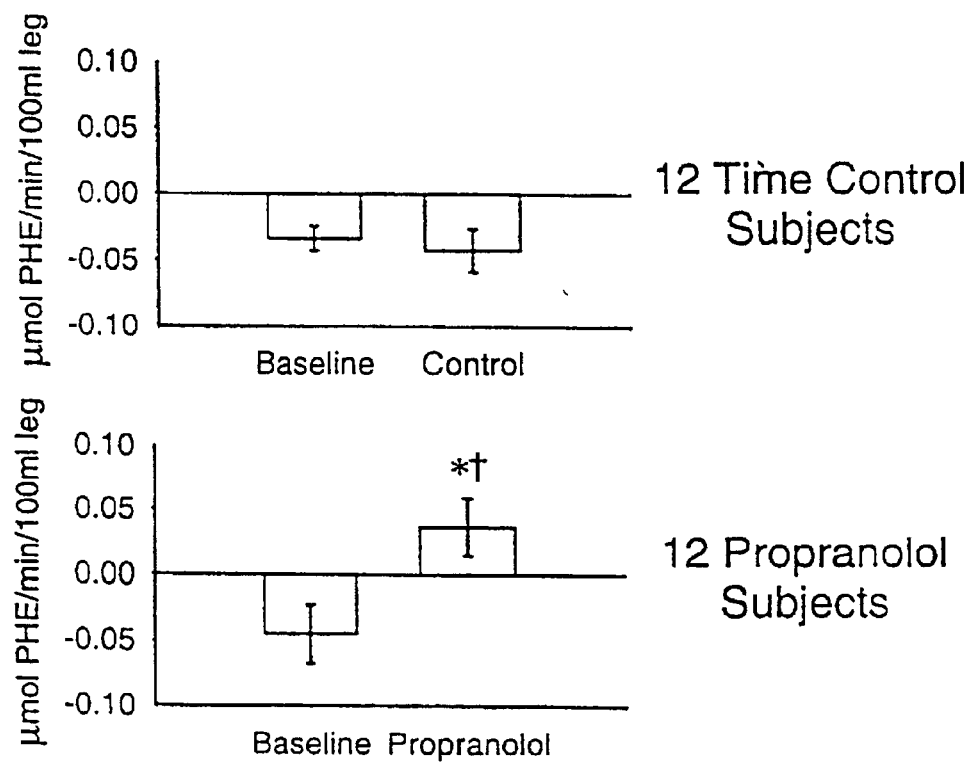
FIG. 2 shows the change in the net balance of muscle protein synthesis and breakdown over two weeks of treatment. *p=0.001 vs non-treated control group by t-test. †p=0.002 vs baseline by paired t-test. Data are presented as mean±SEM.

Concurrent with the decline in energy expenditure, β blockade also improved skeletal muscle protein kinetics. Propranolol administration improved muscle protein net balance from baseline (p=0.005) and as compared with non-treated controls (p=0.001) (FIG. 2). The remainder of the model derived values for the studies comparing propranolol treatment with time control are listed in Table 3. In one of these studies, a steady state of isotope enrichment (tracer/tracee ratio) was not reached, and thus this study was not suitable for analysis. Protein synthesis measured by direct incorporation of the tracer was increased with long-term β-blockade, which was achieved through an increase in synthetic efficiency.

TABLE 3

Skeletal Muscle Protein Kinetics After Treatment

Values reported in μmol Phe/min/100 ml leg unless otherwise noted

| Net Balance of Protein Synthesis and Breakdown | | Non-Treated Controls (n = 12) | Propranolol (n = 12) | p |
|---|---|---|---|---|
| NB | | Protein Synthesis − Protein Breakdown −0.042 ± 0.016 | 0.037 ± 0.022* | 0.001 |
| Model Derived Amino Acid Fluxes | | Non-Treated Controls (n = 12) | Propranolol (n = 11) | |
| $F_{in}$ | Amino Acid Inflow into Leg via Femoral Artery | 0.939 ± 0.175 | 1.085 ± 0.157 | 0.685 |
| $F_{out}$ | Amino Acid Outflow from Leg via Femoral Vein | 0.982 ± 0.180 | 1.034 ± 0.147 | 0.545 |
| $F_{M,A}$ | Inward Transport into Myocyte | 0.145 ± 0.020 | 0.264 ± 0.046† | 0.175 |
| $F_{V,M}$ | Outward Transport from Myocyte | 0.187 ± 0.026 | 0.214 ± 0.042 | 0.671 |
| $F_{V,A}$ | A→V Shunt Past Muscle | 0.795 ± 0.176 | 0.821 ± 0.127 | 0.457 |
| $R_d$ | Rate of Disappearance, Approximating Protein Synthesis | 0.060 ± 0.013 | 0.157 ± 0.027* | 0.012 |
| $R_a$ | Rate of Appearance, Approximating Protein Breakdown | 0.102 ± 0.015 | 0.107 ± 0.019 | 0.671 |
| $F_{O,M}$ | Muscle Protein Synthesis | 0.142 ± 0.034 | 0.337 ± 0.061* | 0.067 |
| $F_{M,O}$ | Muscle Protein Breakdown | | | |

TABLE 3-continued

Skeletal Muscle Protein Kinetics After Treatment

| | | | | |
|---|---|---|---|---|
| $F_{O,M}/(F_{M,A} + F_{M,O})$ | Protein Synthetic Efficiency (%) | 0.184 ± 0.030 | 0.287 ± 0.048† | 0.197 |
| | | 38.7 ± 5.6% | 60.7 ± 3.4%* | 0.028 |
| Fractional Synthetic Rate | Non-Treated Controls (n = 12) | | | |
| FSR | | Rate of Incorporation of Tracer into Muscle over Time (%/hr) 0.24 ± 0.03% | Propranolol (n = 11) 0.34 ± 0.06%† | |

Data presented as mean ± SEM.
\* p < 0.05; † = 0.10 < p < 0.15

Figure 3:
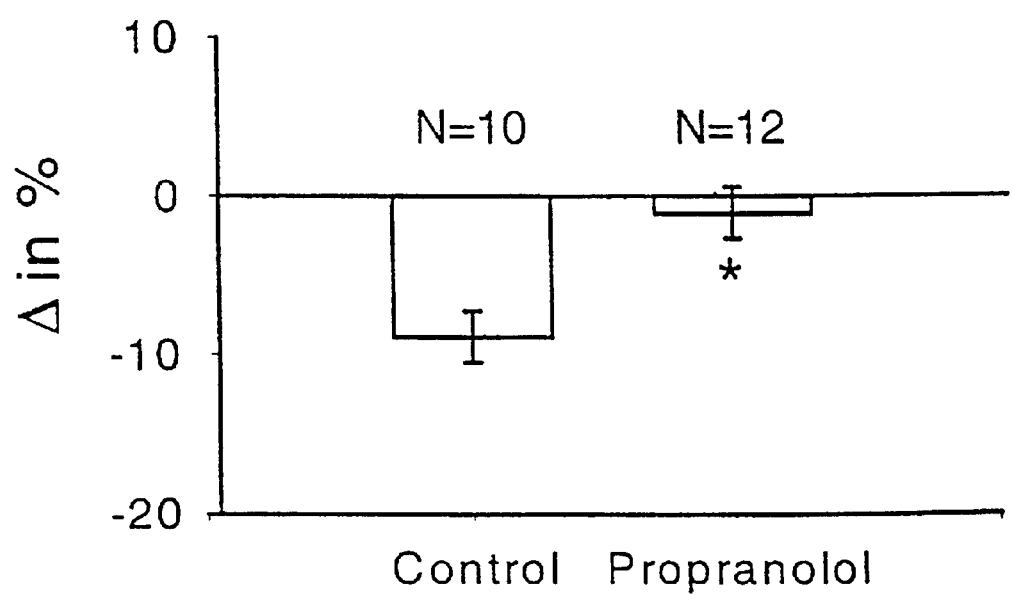
FIG. 3 shows the change in % fat-free mass over 4 weeks of treatment. Each subject's initial K-counter scan before the treatment period was taken as a baseline for comparison with their 4 week K-counter scan. *p<0.01 vs. time control group by t-test. Data are presented as mean±SEM.

Twenty-two subjects underwent a second potassium scintillation scan to evaluate changes in body composition over this time period. The ten control subjects lost approximately 9% of their fat free mass while twelve propranolol subjects lost only 1% (FIG. 3, p=0.003).

Dual image x-ray absorptometry was performed at the time of full healing and discharge from the hospital. This additional measure of lean body mass was performed to serve as an independent correlate of the above changes. Nine consecutive subjects out of the 25 enrolled in the study were not able to undergo DEXA scanning due to technical difficulties with the DEXA scanner over a 3-month period. The remaining 7 subjects in the non-treated control group had a lean body mass percentage of 73.5±1.5%, while the 9 treated with propranol had a percentage of 79.1±1.2%, an approximate 6% improvement (p=0.01).

No negative clinical sequela were found to result from β-blockade. One or more doses of propranolol were held temporarily in 3 of the 13 drug treated subjects for a mean arterial pressure between 60 and 65. These periods were not related to sepsis or operative procedures. Three out of 12 in the non-treated controls developed clinical sepsis at some point during hospitalization, while 4 of 13 in the propranolol group developed sepsis (p=1.0). No other direct or indirect evidence of tissue hypoperfusion—specifically, no intermediate thickness wounds converted to full thickness or metabolic acidosis was found at any time during propranolol treatment. No asthma occurred in any propranolol subject.

Discussion

During catabolism, net muscle protein degradation outweighs net protein synthesis, thus, net protein balance is negative. In this study, stable isotope methodology and serial body composition scanning were applied to show, for the first time, that β blockade with propranolol diminishes skeletal muscle protein wasting seen after severe burn. Out of twenty-five severely burned children studied, thirteen were safely given propranolol and experienced a decrease in resting energy expenditure. Twelve had improved net muscle protein balance. With long-term β-blockade, this translated into greater lean body mass.

Catecholamines are primary mediators of elevated energy expenditure following burn.[5,6,15] Both direct[5,6] and indirect[15] calorimetry have been utilized to demonstrate decreased energy expenditure with β blockade after severe burn. Other studies have also demonstrated decreased urinary nitrogen losses[23] and whole body urea production[24] after β-blockade. Interestingly, β agonism has been shown to stimulate muscle protein synthesis in non-stressed animal models.[25,26] The relevance of these animal models to the physiologic state of critically ill patients is unclear.

The net balance of protein synthesis and breakdown achieved anabolic levels with propranolol treatment. Propranolol's anabolic effect on muscle appears even more dramatic than previous evaluations of other agents reported in burned subjects using similar methodology.[27-29]

To corroborate the results of the stable isotope measurements, two independent body composition tests were employed. Fat-free mass, corresponding to the sum of lean mass and bone mass, was measured by whole body potassium counter before and after four weeks of treatment. In the propranolol group, fat-free mass was preserved (the change was statistically no different than zero). In comparison, ten untreated time control subjects lost 9% of their fat-free mass over this time period. DEXA scans done at the time of discharge in 16 subjects substantiate this result.

Data derived from the stable isotope studies provide insight into the physiologic changes induced by β-blockade at the tissue level. An acceleration in protein synthesis in propranolol treated subjects was seen. Post-traumatic net proteolysis is primarily a result of a large increase in protein degradation, which outweighs a lesser increase in total protein synthesis.[27,30,31] Propranolol induced an increase in the intracellular recycling of free amino acids. In the process of substrate re-utilization, free intracellular amino acids derived from stimulated protein breakdown were re-incorporated back into bound protein without leaving the myocyte.

Each of the methods used to show changes have limitations. For instance, in the stable isotopic studies labeled phenylalanine was used as the only tracer with the assumption that since it is neither synthesized nor degraded in the leg, any changes in phenylalanine net balance reflect total protein balance. This assumption has been verified in normal volunteers, but not in stressed hypermetabolic subjects.[32] Whole body potassium counting assumes that potassium-to-nitrogen ratios of skeletal muscle and non-skeletal muscle are constant. A recent study showed that this may in fact underestimate total lean body mass in conditions of muscle wasting.[33] Dual image x-ray absorptiometry also has its limitations related to total body water, in that it will overestimate lean body mass with edema. Regardless, all three methods agreed, showing significant improvements in lean mass with propranolol treatment despite different assumptions and shortcomings of each method, lending credence to the conclusion that propranolol treatment improves lean mass accretion in severely burned children.

Like any pharmacotherapy, there are risks associated with treatment. Given carelessly, propranolol could cause hypoperfusion from decreased cardiac output, particularly in these who are septic. In others, it could induce severe bronchospasm.

In this study, there was a specific therapeutic goal of decreasing heart rate by 25% (which was previously shown to be safe).[12–14] Subjects were continuously monitored for hemodynamic and respiratory parameters. No related complications were encountered following this administration protocol. Of note, there was no significant decrease in blood pressure with propranolol treatment at these doses. However, propranolol was held in 3 of 13 subjects at same time during the treatment course, dictating close monitoring for patients receiving this treatment. Propranolol treatment does not reduce the ability of these patients to respond to cold stress[34].

Various mechanisms may be at play in the demonstrated changes with propranolol treatment. While the effects may be primary through direct effects on protein flux machinery on diminished β-catecholamine receptor activity, it is also possible that indirect effects are at work though changes in endogenous insulin responsiveness, cortisol activity, or changes in regional blood flow. Further larger studies are required to make these determinations.

In summary, the present invention demonstrates by four independent experimental methods (indirect calorimetry, stable isotopic methodology, whole body potassium scintillation, and dual image x-ray absorptiometry) that long-term β blockade decreases lean mass catabolism in severely burned children. These changes would presumably improve strength and ability to rehabilitate. When dosed to decrease heart rate approximately 20% from pre-treated baseline and evaluated conscientiously, propranolol is a safe, easily administered, and efficacious pharmacotherapy. This therapy has the potential to benefit a wide variety of trauma and general surgical patients who are in negative nitrogen balance.

The following references or patents were cited herein:
1. Monk D N, Plank L D, Franch-Arcas G, Finn P J, Streat S J, Hill G L. Sequential changes in the metabolic response in critically injured patients during the first 25 days after blunt trauma. Ann Surg 1996; 223:395–405.
2. Bessey P Q, Jiang Z M, Johnson D J, Smith R J, Wilmore D W. Posttraumatic skeletal muscle proteolysis: the role of the hormonal environment. World J Surg 1989; 13:465–70.
3. Hart D W, Wolf S E, Mlcak R P, et al. Persistence of muscle catabolism after severe burn. Surgery 2000; 128:312–319.
4. Chang D W, DeSanti L, Demling R H. Anticatabolic and anabolic strategies in critical illness: a review of current treatment modalities. Shock 1998; 10:155–60.
5. Harrison T S, Seaton J F, Feller I. Relationship of increased oxygen consumption to catecholamine excretion in thermal burns. Ann Surg 1967; 165:169–72.
6. Wilmore D W, Long J M, Mason A D, Jr., Skreen R W, Pruitt B A, Jr. Catecholamines: mediator of the hypermetabolic response to thermal injury. Ann Surg 1974; 180:653–69.
7. Goodall M C, Stone C, Haynes B W, Jr. Urinary output of adrenaline and noradrenaline in severe thermal burns. Ann Surg 1957; 145:479.
8. Wilmore D W, Aulick L H. Metabolic changes in burned patients. Surg Clin North Am 1978; 58:1173–87.
9. Asch M J, Feldman R J, Walker H L, et al. Systemic and pulmonary hemodynamic changes accompanying thermal injury. Ann Surg 1973; 178:218–21.
10. Reiss W, Pearson E, Artz CP. The metabolic response to burns. J Clin Invest 1956; 35:62.
11. Newsome T W, Mason A D, Jr., Pruitt B A, Jr. Weight loss following thermal injury. Ann Surg 1973; 178:215–7.
12. Herndon D N, Barrow R E, Rutan T C, Minifee P, Jahoor F, Wolfe R R. Effect of propranolol administration on hemodynamic and metabolic responses of burned pediatric patients. Ann Surg 1988; 208:484–92.
13. Minifee P K, Barrow R E, Abston S, Desai M, Herndon D N. Improved myocardial oxygen utilization following propranolol infusion in adolescents with postburn hypermetabolism. J Pediatr Surg 1989; 24:806–10.
14. Baron P W, Barrow R E, Pierre E J, Herndon D N. Prolonged use of propranolol safely decreases cardiac work in burned children. J Burn Care Rehabil 1997; 18:223–7.
15. Breitenstein E, Chiolero R L, Jequier E, Dayer P, Krupp S, Schutz Y. Effects of beta-blockade on energy metabolism following burns. Burns 1990; 16:259–64.
16. Mangano D T, Layug E L, Wallace A, Tateo I. Effect of atenolol on mortality and cardiovascular morbidity after noncardiac surgery. Multicenter Study of Perioperative Ischemia Research Group. N Engl J Med 1996; 335:1713–20.
17. Hart D W, Wolf S E, Chinkes D L, et al. Determinants of skeletal muscle catabolism after severe burn. Ann Surg 2000; 232:455–465.
18. Biolo G, Chinkes D, Zhang X J, Wolfe R R. Harry M. Vars Research Award. A new model to determine in vivo the relationship between amino acid transmembrane transport and protein kinetics in muscle. JPEN J Parenter Enteral Nutr 1992; 16:305–15.
19. Biolo G, Maggi S P, Williams B D, Tipton K D, Wolfe R R. Increased rates of muscle protein turnover and amino acid transport after resistance exercise in humans. Am J Physiol 1995; 268:E514–20.
20. Ellis K J, Shypailo R J. Total body potassium in the infant. J Radioanal Nucl Chem 1992; 161:61–69.
21. Forbes GB, Lewis AM. Total sodium, potassium, and chloride in adult man. J Clin Invest 1956; 35:596–600.
22. Wells J C, Fuller N J, Dewit 0, Fewtrell M S, Elia M, Cole T J. Four-component model of body composition in children: density and hydration of fat-free mass and comparison with simpler models. Am J Clin Nutr 1999; 69:904–12.
23. Gore D C, Honeycutt D, Jahoor F, Wolfe R R, Herndon D N. Effect of exogenous growth hormone on whole-body and isolated-limb protein kinetics in burned patients. Arch Surg 1991; 126:38–43.
24. Herndon D N, Nguyen T T, Wolfe R R, et al. Lipolysis in burned patients is stimulated by the beta 2-receptor for catecholamines. Arch Surg 1994; 129:1301–4.
25. Eisemann J H, Huntington G B, Ferrell C L. Effects of dietary clenbuterol on metabolism of the hindquarters in steers. J Anim Sci 1988; 66:342–53.
26. MacRae J C, Skene P A, Connell A, Buchan V, Lobley G E. The action of the beta-agonist clenbuterol on protein and energy metabolism in fattening wether lambs. Br J Nutr 1988; 59:457–65.
27. Sakurai Y, Aarsland A, Herndon D N, et al. Stimulation of muscle protein synthesis by long-term insulin infusion in severely burned patients. Ann Surg 1995; 222:283–94; 294–7.
28. Herndon D N, Ramzy P I, DebRoy M A, et al. Muscle protein catabolism after severe burn: effects of IGF-1/IGFBP-3 treatment. Ann Surg 1999; 229:713–20.

29. Hart D W, Wolf S E, Ramzy P I, et al. Anabolic effects of oxandrolone following severe burn. Ann Surg 2001; 233:556–564.
30. Gore D C, Honeycutt D, Jahoor F, Barrow R E, Wolfe R R, Herndon D N. Propranolol diminishes extremity blood flow in burned patients. Ann Surg 1991; 213:568–73.
31. Kien C L, Young V R, Rohrbaugh D K, Burke J F. Increased rates of whole body protein synthesis and breakdown in children recovering from burns. Ann Surg 1978; 187:383–91.
32. Tipton K D, Rasmussen B B, Miller S L, et al. Timing of amino acid-carbohydrate ingestion alters anabolic response of muscle of resistance experience. Am J Physiol 2001; 80 (in press).
33. Wang Z M, Visser M, Ma R, et al. Skeletal muscle mass: evaluation of neutron activation and dual-energy X-ray absorptiometry methods. J Appl Physiol 1996; 80:824–31.
34. Honeycutt D, Barrow R E, Herndon D N. Cold stress response in patients with severe burns after beta-blockade. J Burn Care Rehabil 1992, 13: 181–186.

Any publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method of treating an individual having a severe burn, comprising the step of administering to said individual a pharmacologically effective dose of a beta-adrenergic antagonist, wherein treatment with said beta-adrenergic antagonist improves skeletal muscle protein kinetics in said individual as compared to individual without said treatment.

2. The method of claim 1, wherein said beta-adrenergic antagonist is administered intravenously.

3. The method of claim 2, wherein said beta-adrenergic antagonist is administered in a dose that decrease heart rate in said individual by about 25%.

4. The method of claim 2, wherein said beta-adrenergic antagonist is administered in a dose of from about 0.1 mg/kg of the body weight of the individual to about 10 mg/kg of the body weight of the individual.

5. The method of claim 1, wherein said beta-adrenergic antagonist is selected from the group consisting of propranolol, timolol, nadolol, atenolol, metoprolol, esmolol, nipradilol, carvedilol and acebutolol.

6. The method of claim 1, wherein said beta-adrenergic antagonist is propranolol.

7. The method of claim 6, wherein said propranolol is administered intraveneously in a dose of about 1 mg/kg of the body.

8. A method of treating an individual having a severe burn, comprising the step of administering to said individual a pharmacologically effective dose of propranolol, wherein treatment with said propranolol improves skeletal muscle protein kinetics in said individual as compared to individual without said treatment.

9. The method of claim 8, wherein said propranolol is administered intraveneously.

10. The method of claim 8, wherein said propranolol is administered in a dose that decrease heart rate in said individual by about 25%.

11. The method of claim 8, wherein said propranolol is administered in a dose of from about 0.1 mg/kg of the body weight of the individual to about 10 mg/kg of the body weight of the individual.

* * * * *

UNITED STATES PATENT AND TRADEMARK OFFICE
CERTIFICATE OF CORRECTION

PATENT NO. : 7,098,248 B2 Page 1 of 1
APPLICATION NO. : 09/901429
DATED : August 29, 2006
INVENTOR(S) : David S. Herndon It is certified that error appears in the above-identified patent and that said Letters Patent is hereby corrected as shown below:

On the Title page, in item (*) Notice: Subject to any disclaimer, the term of this patent is extended or adjusted under 35 U.S.C. 154(b) by 443 days, delete "by 443 days" and insert --by 570 days-- therefor.

Signed and Sealed this

Twenty-ninth Day of July, 2008

JON W. DUDAS
*Director of the United States Patent and Trademark Office*